(12) United States Patent
Jeong et al.

(10) Patent No.: US 7,534,899 B2
(45) Date of Patent: May 19, 2009

(54) AROMATIC ENEDIYNE DERIVATIVES, ORGANIC SEMICONDUCTOR THIN FILMS USING THE SAME AND MANUFACTURING METHODS THEREOF, AND ELECTRONIC DEVICES INCORPORATING SUCH FILMS

(75) Inventors: Eun Jeong Jeong, Seongnam-Si (KR); Hyun Sik Moon, Seoul (KR); Kook Min Han, Suwon-Si (KR)

(73) Assignee: Smasung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 11/583,085

(22) Filed: Oct. 19, 2006

(65) Prior Publication Data

US 2007/0120120 A1 May 31, 2007

(30) Foreign Application Priority Data

Nov. 25, 2005 (KR) .................. 10-2005-0113372
Nov. 25, 2005 (KR) .................. 10-2005-0113373

(51) Int. Cl.
*C07D 409/14* (2006.01)
(52) U.S. Cl. ....................................... 549/59
(58) Field of Classification Search ............ 549/59
See application file for complete search history.

(56) References Cited

U.S. PATENT DOCUMENTS 3,686,141 A * 8/1972 Bracke .................. 525/328.1
6,683,782 B2   1/2004 Duva

OTHER PUBLICATIONS

Xi Zhang, Philip E. Eaton, Ian Steele, Richard Gilardi "Nitroacetylene: HCCNO2" Synthesis 2002, No. 14, 2013-2018.*
Katakura, Toshie; Hirai, Katsura; Kita, Hiroshi "Organic semiconductor films for organic thin-film transistors and organic EL devices." Japanese patent JP 2007088115 A.*

Dorwald F. A. Side Reactions in Organic Synthesis, 2005, Wiley: VCH, Weinheim p. IX of Preface.*
Clayden, J. Organolithiums: Selectivity for Organic Synthesis 2002, Pergamon: New York, Chapter 3, 111-147.*
Katz et. al. "Synthetic Chemistry for Ultrapure, Processable, and High-Mobility Organic Transistor Semiconductors" Accounts of Chemical Research 2001, 34, 359-369.*
Ali Afzali et al., "High-Performance Solution-Processed Organic Thin Film Transistors from a Novel Pentacene Precurser" J. Am. Chem. Soc. 2002 vol. 124, p. 8812-8813.
Amanda R. Murphy et al., "Organic Thin Film Transistors from a Soluble Oligothiophene Derivative Containing Thermally Removable Solubilizing Groups" J. Am. Chem. Soc. 2004 vol. 126, p. 1596-1597.

* cited by examiner

*Primary Examiner*—Rita J Desai
*Assistant Examiner*—David K O'Dell
(74) *Attorney, Agent, or Firm*—Harness, Dickey & Pierce, P.L.C.

(57) ABSTRACT

Disclosed are aromatic enediyne derivatives, methods of manufacturing organic semiconductor thin films from such aromatic enediyne derivatives, and methods of fabricating electronic devices incorporating such organic semiconductor thin films. Aromatic enediyne derivatives according to example embodiments provide improved chemical and/or electrical stability which may improve the reliability of the resulting semiconductor devices. Aromatic enediyne derivatives according to example embodiments may also be suitable for deposition on various substrates via solution-based processes, for example, spin coating, at temperatures at or near room temperature to form a coating film that is then heated to form an organic semiconductor thin film. The availability of this reduced temperature processing allows the use of the aromatic enediynes derivatives on large substrate surfaces and/or on substrates not suitable for higher temperature processing. Accordingly, the organic semiconductor thin films according to example embodiments may be incorporated in thin film transistors, electroluminescent devices, solar cells, and memory devices.

2 Claims, 4 Drawing Sheets

AROMATIC ENEDIYNE DERIVATIVES, ORGANIC SEMICONDUCTOR THIN FILMS USING THE SAME AND MANUFACTURING METHODS THEREOF, AND ELECTRONIC DEVICES INCORPORATING SUCH FILMS

BACKGROUND

1. Technical Field

Example embodiments relate to aromatic enediyne derivatives, organic semiconductor thin films formed using such aromatic enediyne derivatives and methods of manufacturing such films, and electronic devices incorporating such organic semiconductor thin films and methods of manufacturing such devices, and, for example, to organic semiconductor thin films fabricated from such aromatic enediyne derivatives that exhibit improved chemical and electrical stability. The aromatic enediyne derivatives according to example embodiments may be applied to substrates via solution-based processes, for example, spin coating, and are suitable for application at or near room temperature to form a coating layer that, after thermal treatment, may form an organic semiconductor thin film on the substrate that may be used in forming a carrier transport layer in an electronic device incorporating such an organic semiconductor thin film.

2. Description of the Related Art

In general, flat display devices, for example, liquid crystal display devices or organic electroluminescent display devices, utilize various thin film transistors during operation. One basic thin film transistor construction comprises a gate electrode formed on a gate dielectric, source/drain electrodes, and a semiconducting channel region formed in a semiconducting material adjacent the gate dielectric and opposite the gate electrode. The conductivity of this semiconducting channel region is, in turn, controlled through operation of the gate electrode. The p-type or n-type semiconductor material forming the channel region serves as a conductive material when the gate electrode is in an "on" state to allow current to flow between the source and drain electrodes and serves as a resistive material when the gate electrode is in an "off" state to suppress leakage current between the source and drain electrodes. The "on" and "off" states of the transistor may correspond to two different voltages that may be alternatively applied to the gate electrode for controlling current flow between the source and drain electrodes.

Although a range of semiconductor materials may be used for forming thin film transistors, amorphous Si (a-Si) and polycrystalline Si (poly-Si) are widely used. As a result of recent trends toward larger areas, lower prices and/or improved flexibility of video displays, various efforts have been directed to manufacturing semiconductors using more flexible organic materials rather than the conventional, relatively expensive and/or rigid inorganic materials, which may require the use of higher-temperature vacuum and/or furnace processes in their formation.

Research into various lower molecular weight organic materials, for example, pentacene, for forming organic semiconductor films is presently ongoing. In this regard, the lower molecular weight organic materials, for example, pentacene, have been reported as having charge mobility in the range of 3.2 to 5.0 $cm^2$/V-s or more and an excellent current on/off ratio. These materials, however, are known to have deficiencies including, for example, the expense associated with forming layers of such materials and difficulty forming a generally uniform layer across large areas of a substrate. These deficiencies are, to some degree, attributable to the need to use expensive vacuum deposition apparatus in forming thin films from these lower molecular weight organic materials and an associated difficulty in forming fine patterns.

Further, oligomeric organic semiconductors, for example, a soluble pentacene precursor, have been reported as suitable for application to a substrate and annealing at about 120 to 200° C. to produce an organic semiconducting layer having a charge mobility of about 0.1 $cm^2$/V-s. In addition, other oligothiophene precursors capable of being applied to a substrate to produce an organic semiconducting layer having a charge mobility of 0.03 to 0.05 $cm^2$/V-s and capable of being annealed at 180 to 200° C., have also been reported. However, such organic semiconductors may be chemically unstable during the subsequent processing necessary to complete the fabrication of a semiconductor device and are accordingly difficult to implement in an actual device manufacturing line. Moreover, results obtained by repeated current-electron sweeping for evaluating electrical stability tends to exhibit a lack of electrical stability that may result in both reduced gate threshold voltage, increased leakage currents and/or reduced reliability of the resulting devices.

Other organic compounds containing an acetylene groups and methods of manufacturing a thin film of such materials through a vacuum deposition process using the organic compound have also been reported. However, the organic compounds and the methods of manufacturing thin films from such organic compounds may require a vacuum deposition process in order to manufacture a thin film. Accordingly, the use of lower molecular weight compounds, for example, pentacene, may be expensive and generally unsuited for preparing organic semiconductor films over a large substrate area for cost-sensitive products.

SUMMARY

Accordingly, aromatic enediyne derivatives have been developed to address one or more deficiencies that have been identified in the conventional art. Compounds according to example embodiments comprise a group of aromatic enediyne derivatives that may be utilized in solution-based application processes, for example, spin coating at room temperature, in order to apply the aromatic enediyne derivative(s) to a variety of substrates to form a coating film. These coating films, which contain one or more of the aromatic enediyne derivatives according to example embodiments, may then be converted into organic semiconductor thin films exhibiting improved chemical and/or electrical stability suitable for fabricating devices having improved functionality and/or reliability.

Example embodiments may also include precursor solutions comprising one or more of the aromatic enediyne derivatives and an organic solvent or organic solvent system useful in the manufacture of organic semiconductor films and devices that incorporate such films.

Example embodiments may also include methods of manufacturing organic semiconductor thin films using a precursor solution incorporating one or more aromatic enediyne derivatives and an organic solvent or solvent system. These precursor solutions may, in turn, be used for forming organic semiconductor thin films.

Example embodiments may also include methods for incorporating organic semiconductor thin films into semiconductor devices in order to produce electronic devices which utilize the organic semiconductor thin film as a carrier transport layer.

BRIEF DESCRIPTION OF THE DRAWINGS

Example embodiments of the aromatic enediyne derivatives, organic semiconductor layers formed from the aromatic enediyne derivatives, active structures incorporating such organic semiconductor layers and semiconductor devices incorporating such active structures are addressed more fully below with reference to the attached drawings in which.

Figure 1:
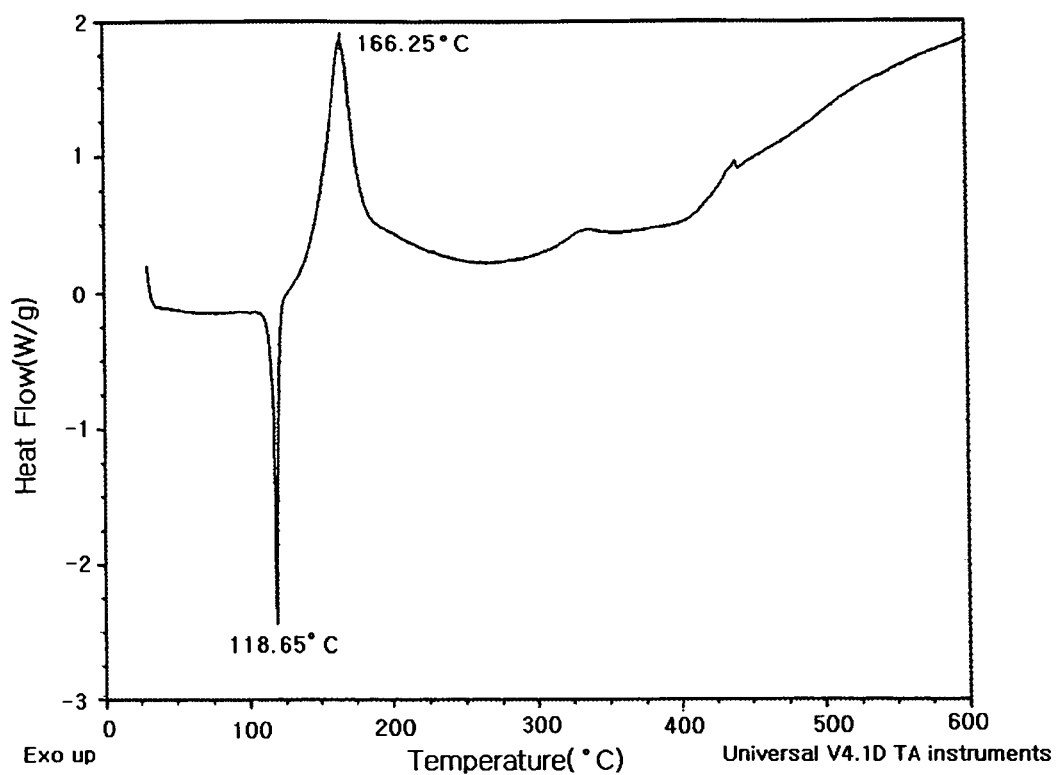
FIG. 1 is a graph showing the result of differential scanning calorimetry (DSC) of an example embodiment of an aromatic enediyne derivative as synthesized in Preparative Example 1 below.
Figure 2:
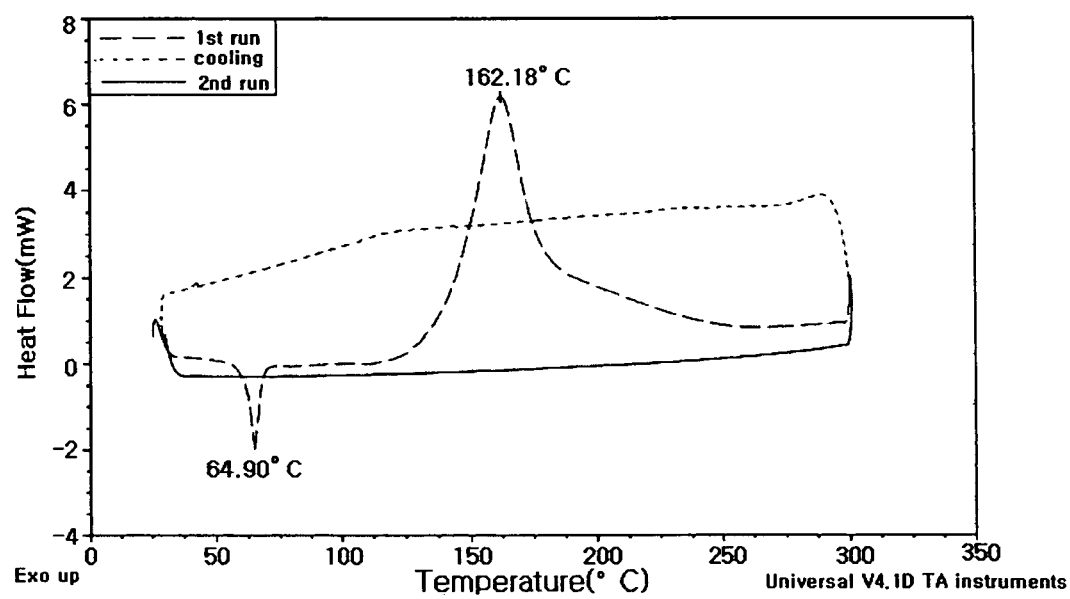
FIG. 2 is a graph showing the result of DSC of an example embodiment of an aromatic enediyne derivative as synthesized in Preparative Example 2 below.
Figure 3:
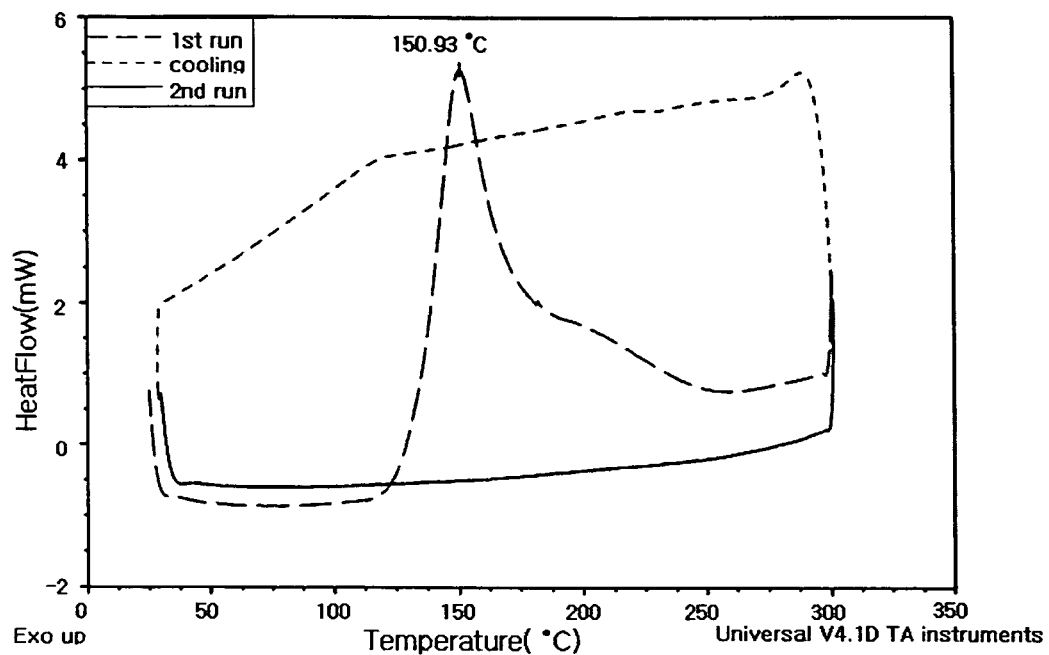
FIG. 3 is a graph showing the result of DSC of an example embodiment of an aromatic enediyne derivative as synthesized in Preparative Example 3 below.
Figure 4:
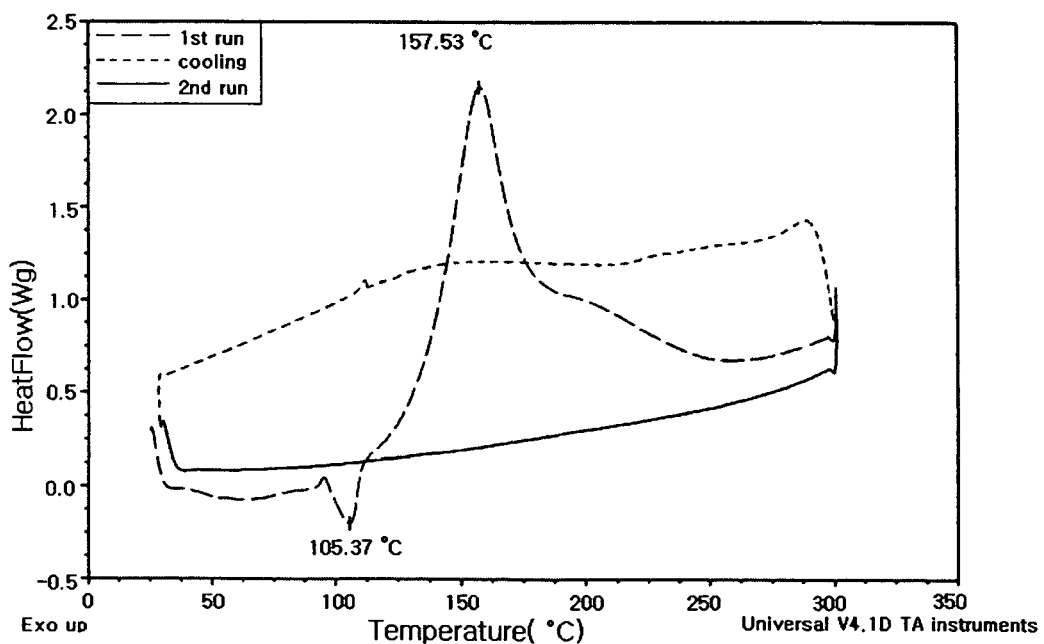
FIG. 4 is a graph showing the result of DSC of an example embodiment of an aromatic enediyne derivative as synthesized in Preparative Example 4 below.

It should be noted that these Figures are intended to illustrate the general characteristics of organic semiconductor compounds and semiconductor device structures according to example embodiments to supplement the written description provided below. These drawings, however, are not necessarily to scale and may not precisely reflect the characteristics of any given embodiment, and should not be interpreted as defining or limiting the range of values or properties of embodiments within the scope of the claims. In particular, the relative positioning and sizing of atoms, bonds, layers or regions may be reduced or exaggerated for clarity.

DESCRIPTION OF EXAMPLE EMBODIMENTS

Various example embodiments of the present invention will now be described more fully with reference to the accompanying drawings in which some example embodiments of the invention are shown. In the drawings, the thicknesses of layers and regions may be exaggerated for clarity.

Detailed illustrative embodiments of the present invention are disclosed herein. However, specific structural and functional details disclosed herein are merely representative for purposes of describing example embodiments of the present invention. This invention may, however, may be embodied in many alternate forms and should not be construed as limited to only the embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the invention to the particular forms disclosed, but on the contrary, example embodiments of the invention are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or" includes any and all combinations of one or more of the associated listed items.

It will be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the FIGS. For example, two FIGS. shown in succession may in fact be executed substantially concurrently or may sometimes be executed in the reverse order, depending upon the functionality/acts involved.

Also, the use of the words "compound," "compounds," or "compound(s)," refer to either a single compound or to a plurality of compounds. These words are used to denote one or more compounds but may also just indicate a single compound.

Now, in order to more specifically describe example embodiments of the present invention, various embodiments of the present invention will be described in detail with reference to the attached drawings. In the figures, if a layer is formed on another layer or a substrate, it means that the layer is directly formed on another layer or a substrate, or that a third layer is interposed therebetween. In the following description, the same reference numerals denote the same elements.

Although example embodiments of the present invention have been disclosed for illustrative purposes, those skilled in the art will appreciate that various modifications, additions and substitutions are possible, without departing from the scope and spirit of the invention as disclosed in the accompanying claims.

Aromatic enediyne derivatives encompassed by example embodiments may be represented by any one of Formulas I to III below:

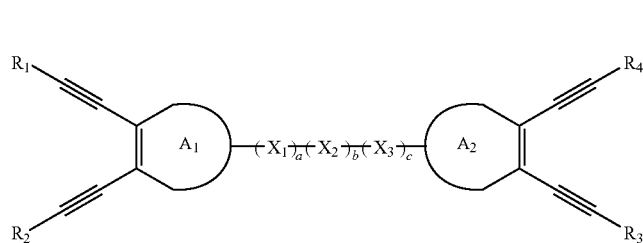

(I)

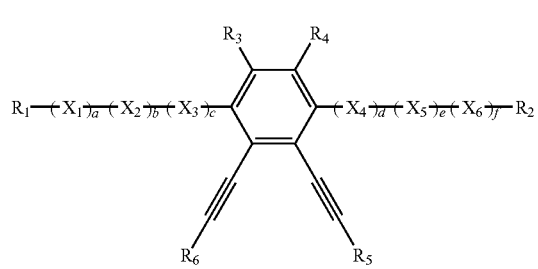

(II)

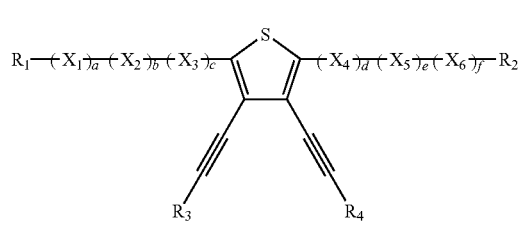

(III)

wherein, in Formulas I to III, $X_1$, $X_2$, $X_3$, $X_4$, $X_5$, $X_6$, $A_1$, and $A_2$ are each independently selected from the group consisting of unsubstituted and unsubstituted C3-C30 arylene groups, and unsubstituted and substituted C2-C30 heteroarylene groups, $R_1$, $R_2$, $R_3$, $R_4$, $R_5$, and $R_6$ are each independently selected from the group consisting of hydrogen, halogen elements, a nitro group, an amino group, a cyano group, —$SiR^1R^2R^3$ (wherein $R^1$, $R^2$, and $R^3$ are each independently selected from a group consisting of hydrogen and C1-C10 alkyl groups), unsubstituted and substituted C1-C20 alkyl groups, unsubstituted and substituted C2-C20 alkenyl group, unsubstituted and substituted C2-C20 alkynyl groups, unsubstituted and substituted C1-C20 alkoxy groups, unsubstituted and substituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, and unsubstituted and substituted C2-C30 heteroarylalkyl groups (in which none of $R_1$, $R_2$, $R_3$, and $R_4$ are hydrogen in Formula I, neither $R_5$ and $R_6$ are hydrogen in Formula II, and neither $R_3$ and $R_4$ are hydrogen in Formula III), and a, b, c, d, e, and f are each independently an integer from 0 to 10 inclusive, and further wherein the expressions (a+b+c)> 0 and, if applicable, (d+e+f)>0, are both satisfied.

A plastic substrate, for example, those used in fabricating flexible display devices, may not endure a heat-curing temperature greater than 150° C., thus causing problems related to light weight and/or flexibility. Lower molecular weight aromatic enediyne derivatives according to example embodiments may form an organic semiconductor material having linear conjugated chains, which may be used to manufacture an organic semiconductor thin film. Further, example embodiments of organic semiconductor materials use a solution-based process at lower temperatures, leading to an organic semiconductor thin film having regular molecular arrangement of the lower molecular semiconductor material and electrical stability of the polymer.

In aromatic enediyne derivatives according to example embodiments, two acetylene groups may be bound to a double bond of an aromatic substituent to form an unsaturated core. Thus, the aromatic enediyne derivative may be advantageous because it has a specific chemical structure and active mechanism making it suitable for realizing higher reactivity, and thus a radical benzene ring may be more easily formed even at lower temperatures, thereby realizing polymerization through intermolecular bonding.

In the aromatic enediyne derivatives of Formulas I to III, $X_1$, $X_2$, $X_3$, $X_4$, $X_5$, $X_6$, $A_1$, and $A_2$, may each be independently selected from the groups represented by the formulae illustrated below. The carrier mobility in the resulting organic semiconductor layer appears to be a function of the thiophene and/or phenyl groups in order to increase the mobility of a semiconductor.

The $X_1$, $X_2$, $X_3$, $A_1$, and $A_2$ in Formula I may include at least two thiophene rings.

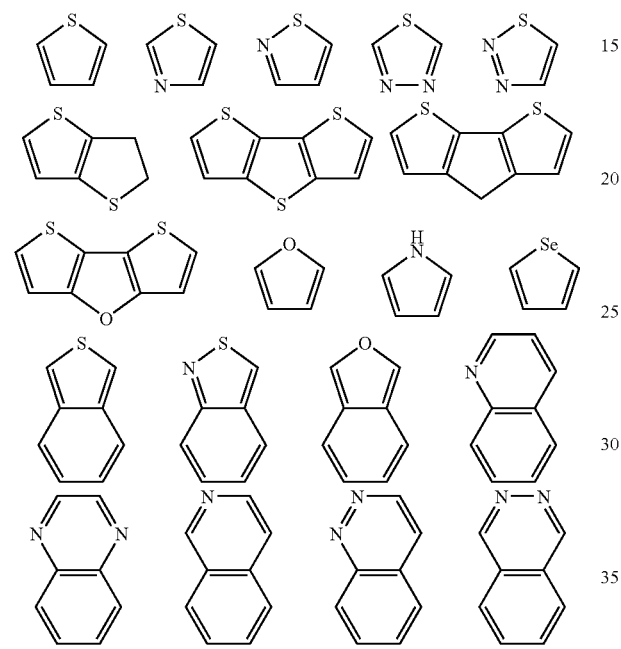

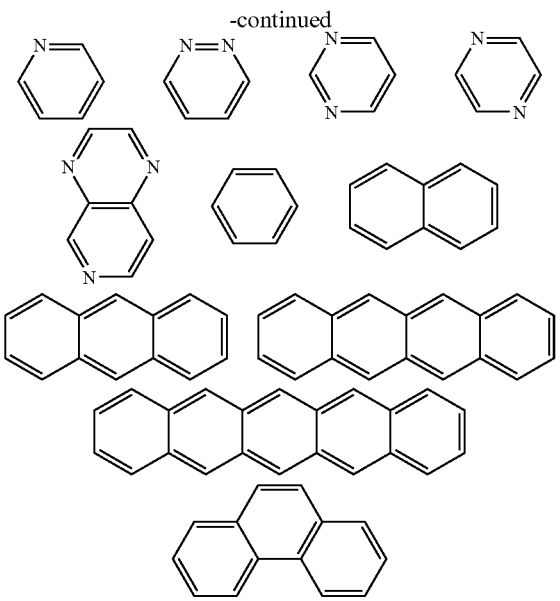

(in which the $A_1$ and $A_2$ in Formula I are not

(1,3,4-thiadiazole)).

Specifically, example embodiments of aromatic enediyne derivatives include those compounds represented below in Formula V and Formula VI:

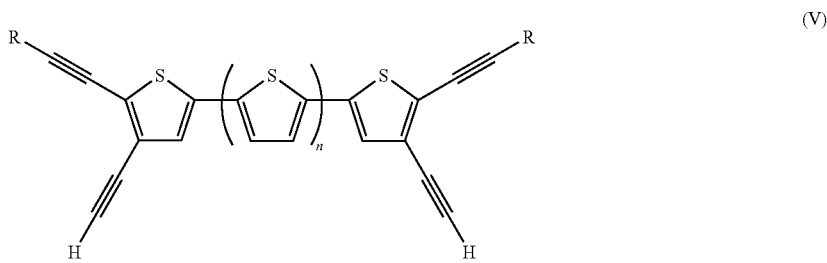

(V)

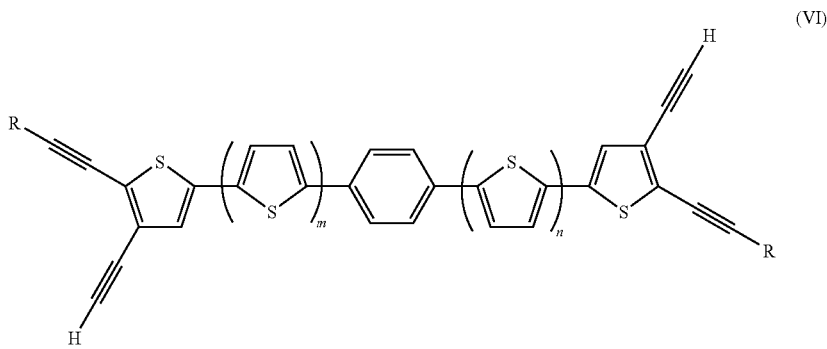

(VI)

in Formulas V and VI, R is selected from the group consisting of halogen elements, a nitro group, an amino group, a cyano group, —SiR¹R²R³ (where R¹, R², and R³ are each independently selected from a group consisting of hydrogen and C1-C10 alkyl groups), unsubstituted and substituted C1-C20 alkyl groups, unsubstituted and substituted C2-C20 alkenyl groups, unsubstituted and substituted C2-C20 alkynyl groups, unsubstituted and substituted C1-C20 alkoxy groups, unsubstituted and substituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, and unsubstituted and substituted C2-C30 heteroarylalkyl groups, and m and n are each an integer from 1 to 10 inclusive.

More specifically, example embodiments of aromatic enediyne derivatives include compounds corresponding to Formulas VII to X below:

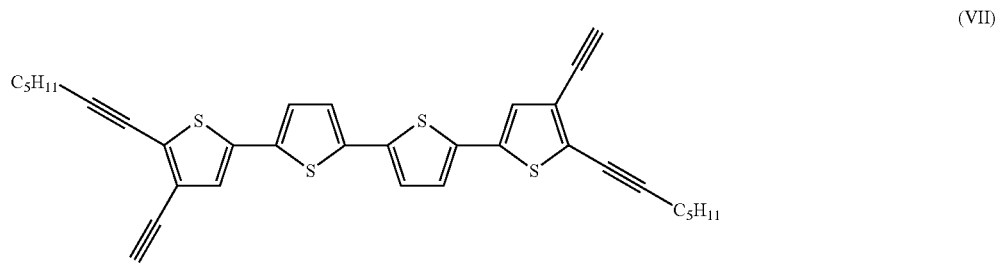

(VII)

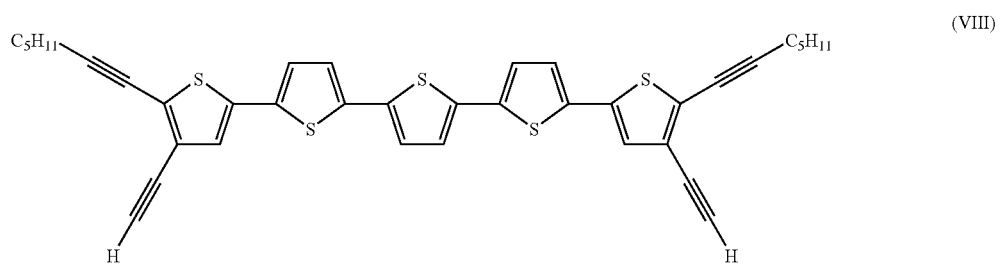

(VIII)

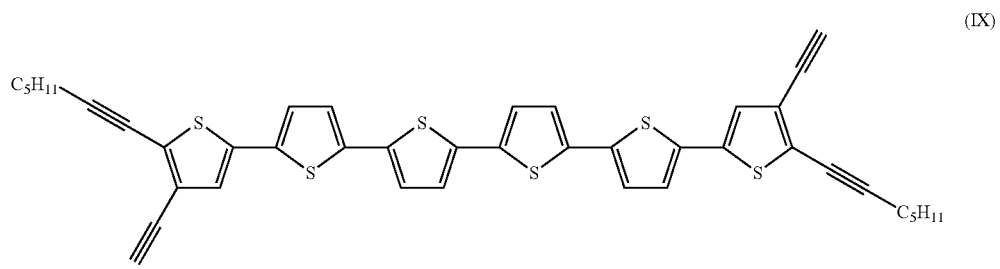

(IX)

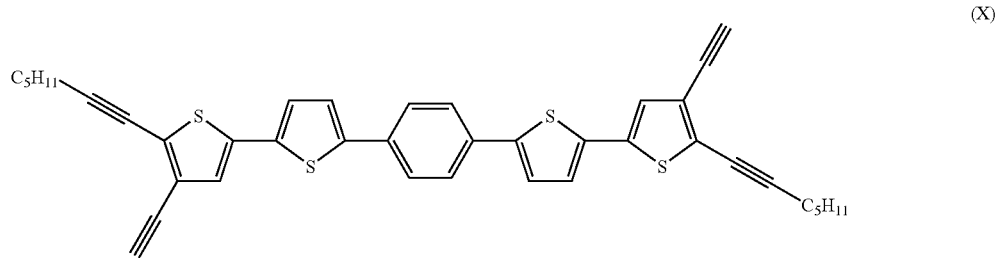

(X)

Aromatic enediyne derivatives according to example embodiments may be formed using any suitable synthesis process(es) and are not limited by the manner in which they are formed.

One or more such aromatic enediyne derivatives may be used as material for forming an organic semiconductor active layer and thus may be effectively incorporated in the fabrication of various electronic devices, for example, thin film transistors, electroluminescent devices, solar cells, and memory devices.

In addition, example embodiments provide for precursor solutions that may be used in the fabrication of an organic semiconductor, comprising one or more aromatic enediyne derivatives and an organic solvent or organic solvent system.

In a precursor solution, an aromatic enediyne derivative may be used in the form of a combination of two or more of aromatic enediyne derivatives represented by Formulas I to III. Further, the aromatic enediyne derivative(s) incorporated in the precursor solution may be present in an amount of 0.01 to 30 wt % based on the total weight of the solution.

An organic solvent or solvent system used in forming a precursor solution may include at least one solvent selected from a group consisting of aliphatic hydrocarbon solvents, for example, hexane and heptane; aromatic hydrocarbon solvents, for example, toluene, pyridine, quinoline, anisol, mesitylene and xylene; ketone-based solvents, for example, methyl isobutyl ketone, 1-methyl-2-pyrrolidinone, cyclohexanone or acetone; ether-based solvents, for example, tetrahydrofuran or isopropyl ether; acetate-based solvents, for example, ethyl acetate, butyl acetate or propylene glycol methyl ether acetate; alcohol-based solvents, for example, isopropyl alcohol or butyl alcohol; amide-based solvents, for example, dimethylacetamide or dimethylformamide; silicon-based solvents, and mixtures thereof.

In addition, example embodiments may include methods of manufacturing organic semiconductor thin films, comprising i) applying a precursor solution to a substrate to form a coating film; and ii) heating the coating film to a treatment temperature and for a time period sufficient to initiate crosslinking of aromatic enediyne derivative(s), thus forming a thin film.

The substrate on which the organic semiconductor thin film is formed is not particularly limited so long as it does not interfere with the intended use or processing of aromatic enediyne derivatives or the precursor solutions incorporating such derivatives, and may, for example, be selected from a group including glass substrates, silicon wafers, ITO glass, quartz, a silica-coated substrates, alumina-coated substrates, plastic substrates, etc., depending on the demands and requirements of the intended end use for the resulting devices.

Useful processes for applying the precursor solution to the substrate for form a coating film include spin coating, dip coating, roll-to-roll coating, screen coating, spray coating, spin casting, flow coating, screen printing, ink jet coating and drop casting. Of these coating processes, it is anticipated that spin coating processes may be easily integrated into a semiconductor fabrication process and is capable of producing sufficiently uniform coating layers over large substrate areas. The actual sequences utilized in such spin coating processes may vary somewhat, but it is anticipated that spin coating processes utilizing a spin speed in the range from 100 to 10,000 rpm will be capable of producing acceptable coating films on most substrates.

Subsequently, the coating film may be subjected to a thermal treatment to promote crosslinking and the polymerization of aromatic enediyne derivative(s) contained therein, thereby obtaining a desired organic semiconductor thin film. Depending on the substrate material and the particular aromatic enediyne derivative(s) and organic solvent(s) utilized in a particular application, the thermal treatment may be conducted at a treatment temperature of 100 to 250° C.

The duration of the thermal treatment may range from 1 to 100 minutes and may be conducted under a generally uniform temperature or may be conducted under varying temperatures, for example, with the treatment temperature gradually increasing over the duration of the thermal treatment or with more complex temperature profiles including, for example, a temperature ramp up, followed by a hold period, followed by a temperature ramp down. As will be appreciated by those skilled in the ant, the pressure and gas content to which the coating film is exposed during the thermal treatment may also be varied throughout the course of the treatment to provide, for example, increased solvent removal during the early portions of the treatment and suppressed oxidation during the later portions of the treatment through the varied application of vacuum and the use of one or more inert or less reactive gases.

The crosslinking mechanism of aromatic enediyne derivatives is represented by the Reaction 1 illustrated below:

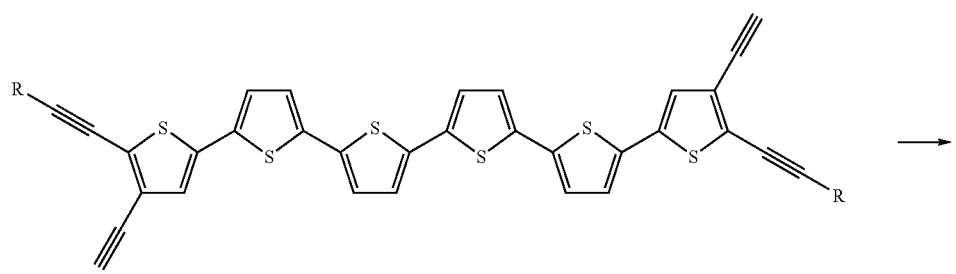

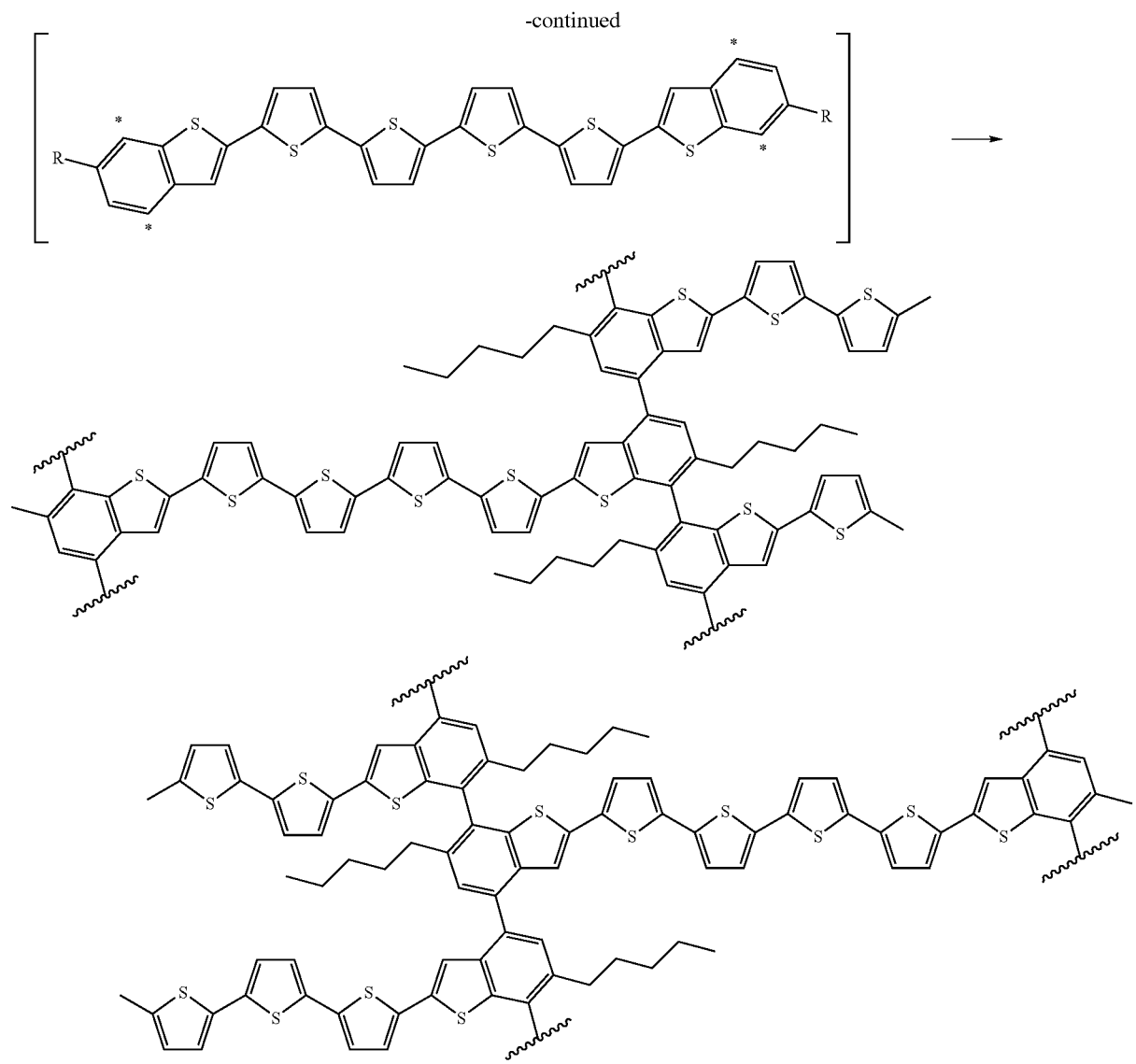

As is apparent from Reaction 1, the acetylene groups bound to the double bonds of an aromatic enediyne derivative are formed into radical benzene rings at a predetermined or desired reaction temperature thanks to higher reactivity of the active mechanism of enediyne, resulting in a polymer network through intermolecular bonding.

In the case where a semiconductor thin film is formed using a conventional precursor solution, the thin film may crack due to the emission of gas created by the intermolecular bonding or solvent during the heat treatment. However, the organic semiconductor thin film according to example embodiments is polymerized through the radical reaction using the higher reactivity of the active mechanism of enediyne, thereby reducing or preventing the cracking of the thin film, which may be caused by the generation of gas during a continuous process. Moreover, the crosslinking reaction progresses without the use of an additive, thus reducing or preventing a negative effect capable of interrupting the molecular arrangement due to the use of the additive acting as an impurity.

The organic semiconductor thus formed may maintain improved transistor properties due to intermolecular packing based on the regular arrangement of a monomolecular aromatic enediyne derivative and intermolecular cross-network formation, and may also assure chemical and electrical stability and reliability upon formation into a polymeric thin film. In the case where the organic semiconductor is applied as the carrier transport layer to electronic devices, improved properties may be provided and the cost reduction effect may be improved or maximized by adopting a room-temperature solution-based process.

Specific examples of the electronic device that may include organic semiconductor regions formed from aromatic enediyne derivatives include organic thin film transistors, electroluminescent devices, solar cells, and memory devices. Aromatic enediyne derivatives according to example embodiments may be applied as a solution or precursor composition to substrates used in forming these or other devices using conventional coating processes.

A better understanding of example embodiments may be obtained in light of the following examples which are set forth to illustrate, but should not to be construed to limit, the disclosure.

PREPARATIVE EXAMPLE 1
Synthesis of Example Aromatic Enediyne Derivative A
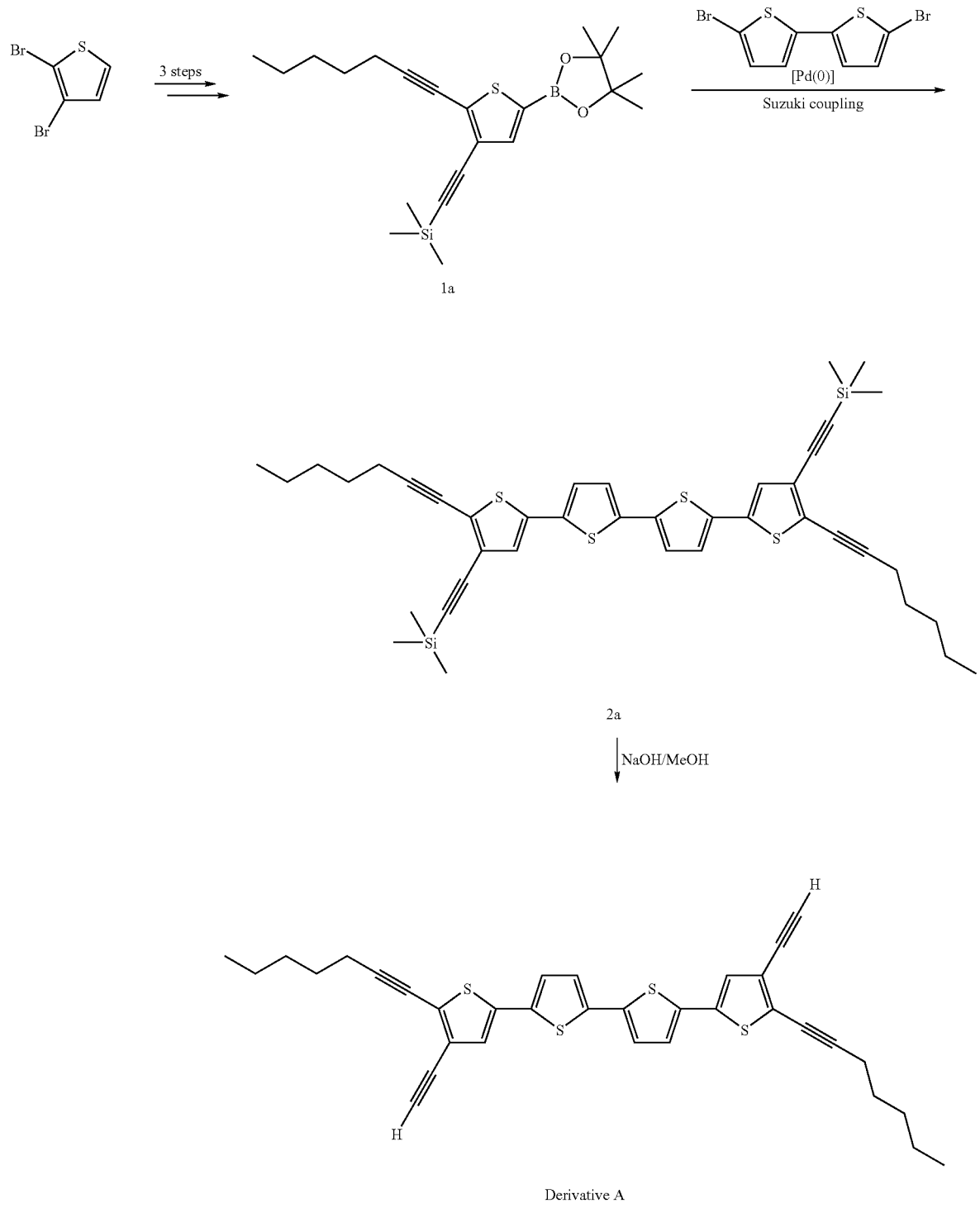

2 ml (18.0 mmol) of 2,3-dibromothiophene, commercially available from Aldrich under the Product No. D4,390-5, and 3.5 ml (27.0 mmol) of 1-heptyne, commercially available from Aldrich under the Product No. 24, 441-4, were mixed with a solvent of tetrahydrofuran/diisopropylamine (1:1), and 0.23 g (0.36 mmol) of palladium dichlorodiphosphine, 70 mg (0.36 mmol) of copper iodide and 0.1 g (0.36 mmol) of triphenylphosphine were sequentially added thereto. The reaction solution was heated at 70° C. for 8 hours, and washed with an aqueous solution of ammonium chloride. The resulting organic layer was dried over magnesium sulfate, dried under reduced pressure, and purified using silica gel column chromatography, thus obtaining 4.6 g of 2-heptynyl 3-bromothiophene. The compound thus obtained was added with 3.3 ml (23.2 mmol) of trimethylsilylacetylene, commercially available from Aldrich under the Product No. 21, 817-0 and then subjected to the above synthesis process, to prepare 2.7 g (9.84 mmol) of 2-heptynyl-3-trimethylsilylethynylthiophene, which was then mixed with 12.8 ml (12.8 mmol) of lithium diisopropylamide (1 M) at about −78° C. The reaction mixture was stirred at the same temperature for 30 minutes, then combined with 2.4 ml (11.8 mmol) of 2-isopropoxy-4,4,5,5-tetramethyl-1,3,2-dioxaborolane, commercially available from Aldrich under the Product No. 41,714-9, and allowed to react in a bath while the temperature was increased to room temperature. The resultant reaction solution was poured into an aqueous solution of 1 N HCl, treated with chloroform to obtain an organic layer, which was then dried over magnesium sulfate 1 N HCl, treated with chloroform to obtain an organic layer, which was then dried over magnesium sulfate and distilled under reduced pressure, thus obtaining 4.1 g of a compound 1a in an oil phase. Analysis of the compound 1a produced the following NMR data: $^1$H NMR (300 MHz, CDCl$_3$), δ(ppm) 0.24 (s, 9H), 0.92 (t, 3H, J=7.2 Hz), 1.24-1.64 (m, 18H), 2.49 (t, 2H, J=7.0 Hz), 7.47 (s, 1H).

0.5 g (1.54 mmol) of 2,2'-dibromo-5,5'-bithiophene and 1.6 g (4.00 mmol) of borolane 1a were added to toluene and water, and then a Pd(PPh$_3$)$_4$ [(tetrakis(triphenylphosphine) palladium)(0)(Aldrich)] catalyst and potassium carbonate were added thereto, after which the reaction mixture was allowed to react at 110° C. for 8 hours and then washed with an aqueous solution of 1 N HCl. The resulting organic layer was dried and purified using silica gel column chromatography, thus obtaining 0.64 g (58%) of a compound 2a. Analysis of the compound 2a produced the following NMR data: $^1$H NMR (300 MHz, CDCl$_3$), δ(ppm) 0.26 (s, 18H), 0.93 (t, 6H, J=7.2 Hz), 1.24-1.67 (m, 12H), 2.50 (t, 4H, J=7.0 Hz), 7.05 (d, 4H, J=2.8 Hz), 7.34 (s, 2H)

0.54 g of the compound 2a was dissolved in chloroform/methylalcohol (having a volume ratio of ⅓) and then added with 1 g of NaOH, and the reaction mixture was stirred for 10 min. The stirred reaction solution was washed with an aqueous solution of 1 N HCl, and the organic layer was dried and purified using silica gel column chromatography, thus yielding 0.3 g of the derivative A. Analysis of the derivative A material produced the following NMR data: $^1$H NMR (300 MHz, CDCl$_3$), δ(ppm) 0.93 (t, 6H, J=7.1 Hz), 1.35-1.67 (m, 12H), 2.51 (t, 4H, J=7.0 Hz), 3.26 (s, 2H), 7.05-7.07 (m, 6H).

PREPARATIVE EXAMPLE 2

Synthesis of Example Aromatic Enediyne Derivative B

Preparative Example 2: Synthesis of Example Aromatic Enediyne Derivative B

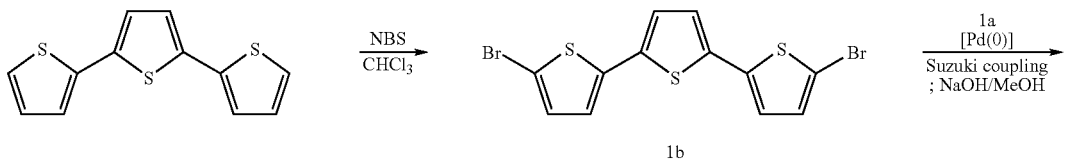

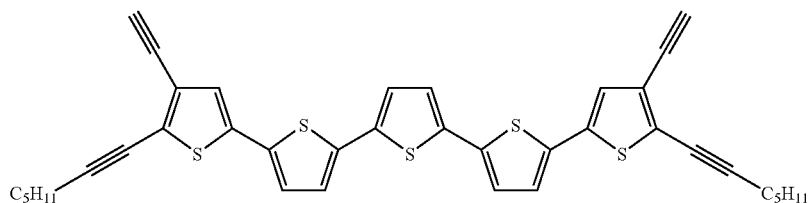

Derivative B 0.25 g (1 mmol) of 2,2':5',2''-terthiophene, commercially available from Aldrich under the Product No. 31, 107-3, was added to chloroform, and 0.35 g (2.0 mmol) of N-bromosuccinimide was added thereto, thus obtaining dibromide 1b, which was then subjected to Suzuki coupling and desilylation under the same synthetic conditions as in the synthesis of the derivative A, thereby yielding the derivative B. Analysis of the derivative B produced the following NMR data: $^1$H NMR (300 MHz, CDCl$_3$), δ(ppm) 0.93 (t, 6H, J=7.2 Hz), 1.24-1.67 (m, 12H), 2.51 (t, 4H, J=7.0 Hz), 3.26 (s, 2H), 7.05-7.08 (m, 8H).

PREPARATIVE EXAMPLE 3

Synthesis of Example Aromatic Enediyne Derivative C

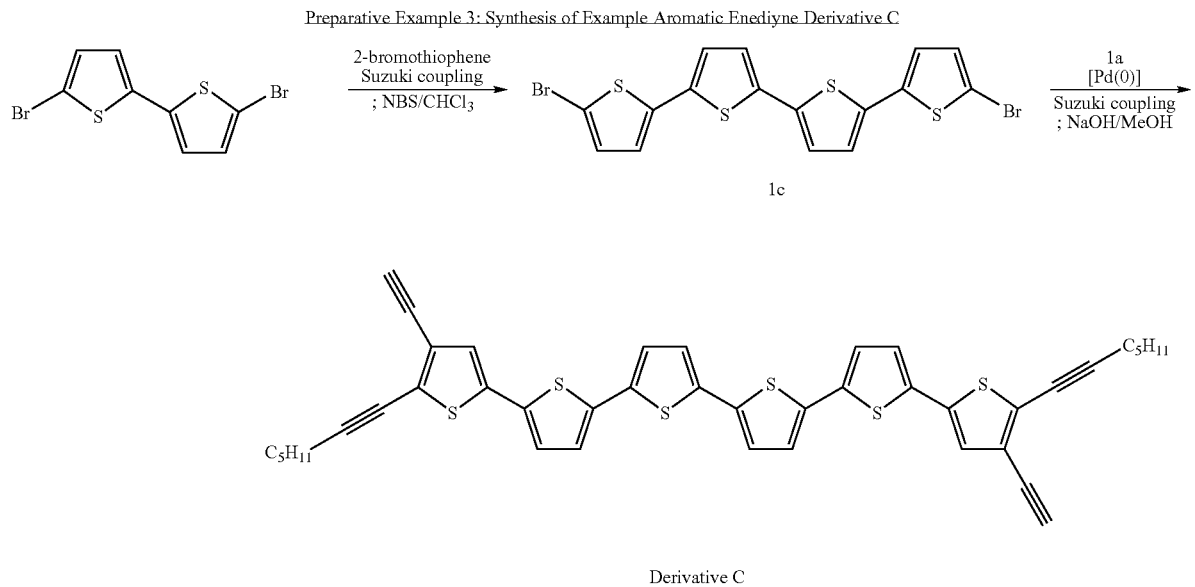

5,5'-dibromo-2,2'-bithiophene, commercially available from Aldrich under the Product No. 51.549-3, and 2-thiopheneboronic acid, commercially available from Aldrich under the Product No. 43, 683-6, were subjected to Suzuki coupling, thus obtaining a predetermined or desired product, which was then added with N-bromosuccinimide to prepare dibromotetrathiophene 1c. Subsequently, the compound 1c was subjected to Suzuki coupling and desilylation under the same synthetic conditions as in the synthesis of the derivative A, therefore yielding the derivative C. Analysis of the derivative C produced the following NMR data: $^1$H NMR (300 MHz, CDCl$_3$), δ(ppm) 0.93 (t, 6H, J=7.2 Hz), 1.24-1.67 (m, 12H), 2.51 (t, 4H, J=7.0 Hz), 3.27 (s, 2H), 7.05-7.09 (m, 10H).

PREPARATIVE EXAMPLE 4

Synthesis of Example Aromatic Enediyne Derivative D

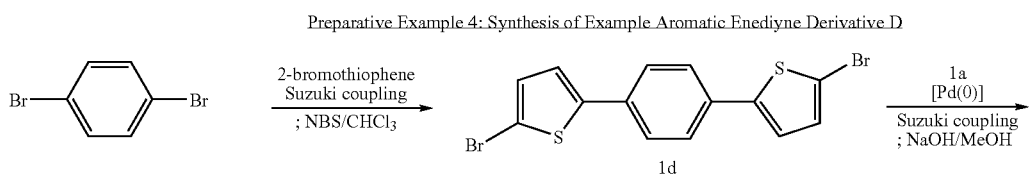

-continued

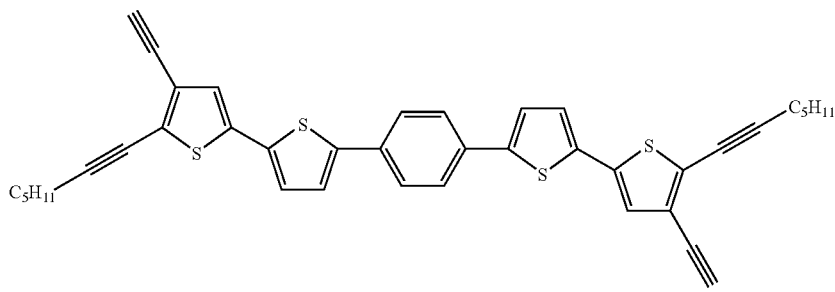

Derivative D 1 g (4.2 mmol) of 1,4-dibromobenzene, commercially available from Aldrich under the Product No. D3,902-9, was subjected to Suzuki coupling with 2-bromothiophene, to prepare 0.72 g (3.0 mmol) of a predetermined or desired product, which was then added to chloroform, and 1.1 g (6.2 mmol) of N-bromosuccinimide was added thereto, thus preparing 0.6 g of dibromide 1d. Subsequently, the compound 1d was subjected to Suzuki coupling and desilylation under the same synthetic conditions as in the synthesis of the derivative A, therefore yielding the derivative D. Analysis of the derivative D produced the following NMR data: $^1$H NMR (300 MHz, CDCl$_3$), δ(ppm) 0.93 (t, 6H, J=7.2 Hz), 1.24-1.67 (m, 12H), 2.51 (t, 4H, J=7.0 Hz), 3.27 (s, 2H), 7.01 (s, 2H), 7.13 (d, 2H, J=3.8 Hz), 7.25 (d, 2H, J=3.8 Hz), 7.60 (s, 4H).

PREPARATIVE EXAMPLE 5

Synthesis of Example Aromatic Enediyne Derivative IIc

Preparative Example 5: Synthesis of Example Aromatic Enediyne Derivative IIc

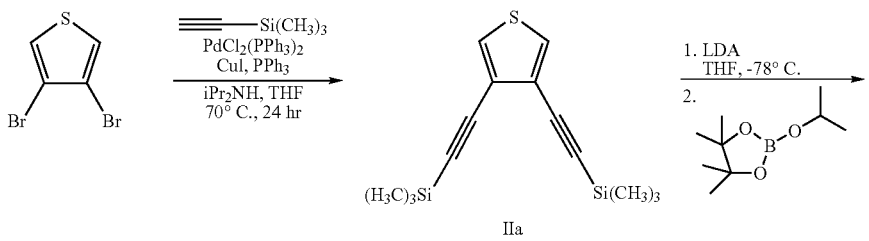

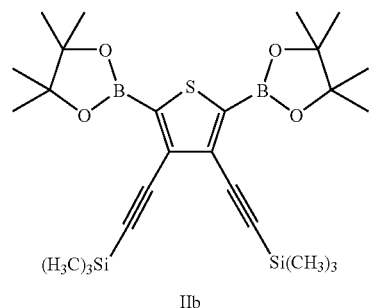

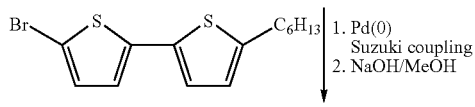

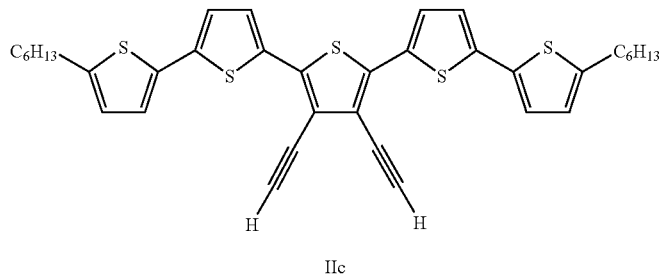

IIc 2.5 ml (22.6 mmol) of 3,4-dibromothiophene, commercially available from Aldrich under the Product No. 24, 715-4, and 8 ml (56.5 mmol) of trimethylsilylacetylene were mixed with a solvent of tetrahydrofuran/diisopropylamine (1:1), and 0.15 g (0.23 mmol) of palladium dichlorodiphosphine, 21 mg (0.11 mmol) of copper iodide and 0.1 g (0.36 mmol) of triphenylphosphine were then sequentially added thereto. The reaction solution was heated at 70° C. for 8 hours, and washed with an aqueous solution of ammonium chloride. The resulting organic layer was dried over magnesium sulfate, dried under reduced pressure, and purified using silica gel column chromatography, thus obtaining 1.5 g of 3,4-bis(trimethylsilylethynyl)thiophene (IIa).

1 g (3.62 mmol) of 3,4-bis(trimethylsilylethynyl)thiophene, which was then mixed with 10.8 ml (10.8 mmol) of lithium diisopropylamine (LDA) (1 M) at about −78° C. The reaction mixture was stirred at the same temperature for 30 minutes, then combined with 2.4 ml (11.8 mmol) of 2-isopropoxy-4,4,5,5-tetramethyl-1,3,2-dioxaborolane, commercially available from Aldrich under the Product No. 41, 714-9, and allowed to react in a bath while the temperature was increased to room temperature. The resultant reaction solution was poured into an aqueous solution of 1 N HCl, treated with chloroform to obtain an organic layer, which was then dried over magnesium sulfate 1 N HCl, treated with chloroform to obtain an organic layer, which was then dried over magnesium sulfate and distilled under reduced pressure, thus obtaining 2.1 g of a compound diborolane in an oil phase.

2.96 g (9.0 mmol) of 2-bromo-2'-hexyl-5,5'-bithiophene and 2.1 g (4.0 mmol) of borolane were added to toluene and water, and then a Pd(PPh₃)₄ [(tetrakis(triphenylphosphine)palladium)(0)(Aldrich)] catalyst and potassium carbonate were added thereto, after which the reaction mixture was allowed to react at 110° C. for 8 hours and then washed with an aqueous solution of 1 N HCl. The resulting organic layer was dried and purified using silica gel column chromatography, thus obtaining 1.55 g (51%) of a compound IIb.

1.55 g of the compound IIb was dissolved in chloroform/methylalcohol (having a volume ratio of ⅓) and then added with 1 g of NaOH, and the reaction mixture was stirred for 10 min. The stirred reaction solution was washed with an aqueous solution of 1 N HCl, and the organic layer was dried and purified using silica gel column chromatography, thus yielding 1.01 g of the derivative IIc.

Analysis of the derivative A material produced the following NMR data: 1H NMR (300 MHz, CDCl₃), δ(ppm) 0.88 (1, 6H, J=6.7 Hz), 1.24-1.45 (m, 12H), 1.64-1.69 (m, 4H), 2.77 (1, 4H, J=7.5 Hz), 3.27 (s, 2H), 7.03-7.07 (m, 8H).

PREPARATIVE EXAMPLE 6

Synthesis of Example Aromatic Enediyne Derivative IIIc

Preparative Example 6: Synthesis of Example Aromatic Enediyne Derivative IIc

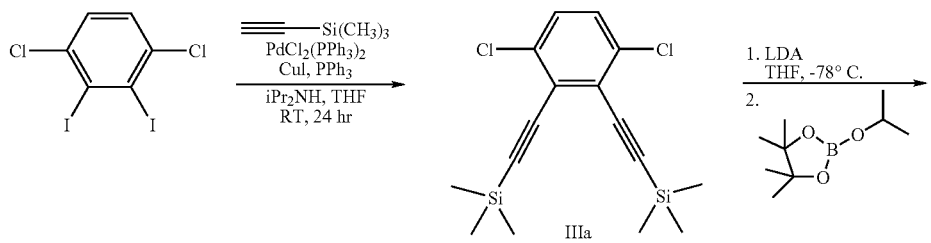

IIIa

-continued

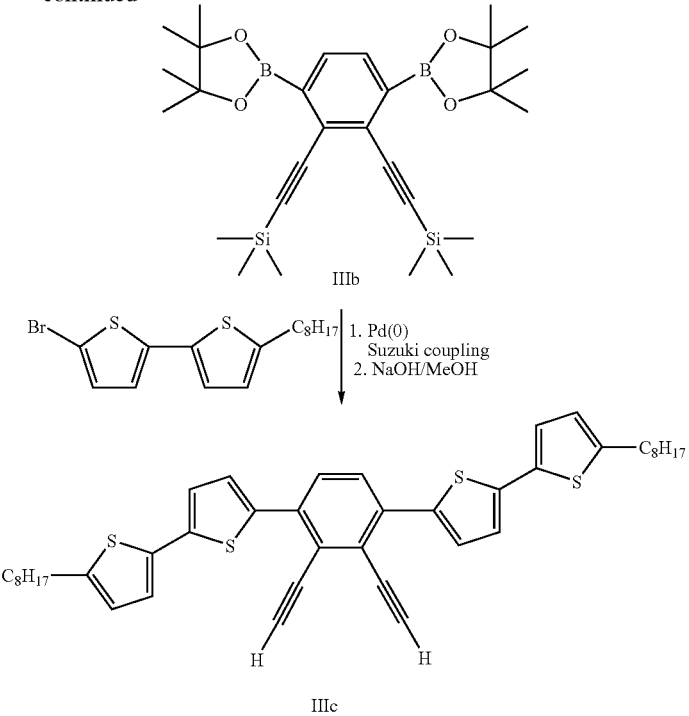

3 g (7.5 mmol) of 1,4-dichloro-2,3-diiodobenzene (Chirogenix Co.) and 1.5 ml (15.0 mmol) of trimethylsilylacetylene were mixed with a solvent of tetrahydrofuran/diisopropylamine (1:1), and 0.15 g (0.23 mmol) of palladium dichlorodiphosphine, 21 mg (0.11 mmol) of copper iodide and 0.1 g (0.36 mmol) of triphenylphosphine were sequentially added thereto. The reaction solution was heated at 70° C. for 8 hours, and washed with an aqueous solution of ammonium chloride. The resulting organic layer was dried over magnesium sulfate, dried under reduced pressure, and purified using silica gel column chromatography, thus obtaining 1.27 g of 1,4-dichloro-2,3-bis(trimethylsilylacetylene)benzene (IIIa).

1.27 g (3.75 mmol) of 1,4-dichloro-2,3-bis(trimethylsilylacetylene)benzene, which was then mixed with 7.5 ml (7.5 mmol) of lithium diisopropylamine (1 M) at about −78° C. The reaction mixture was stirred at the same temperature for 30 minutes, then combined with 1.6 ml (7.5 mmol) of dioxaborolane and allowed to react in a bath while the temperature was increased to room temperature. The resultant reaction solution was poured into an aqueous solution of 1 N HCl, treated with chloroform to obtain an organic layer, which was then dried over magnesium sulfate 1 N HCl, treated with chloroform to obtain an organic layer, which was then dried over magnesium sulfate and distilled under reduced pressure, thus obtaining 1.8 g of a compound diborolane in an oil phase.

2.80 g (8.5 mmol) of 2-bromo-2'-hexyl-5,5'-bithiophene and 1.8 g (3.4 mmol) of borolane were added to toluene and water, and then a Pd(PPh$_3$)$_4$ [(tetrakis(triphenylphosphine)palladium)(0)(Aldrich)] catalyst and potassium carbonate were added thereto, after which the reaction mixture was allowed to react at 110° C. for 8 hours and then washed with an aqueous solution of 1 N HCl. The resulting organic layer was dried and purified using silica gel column chromatography, thus obtaining 1.28 g (49%) of a compound IIb.

1.28 g of the compound IIb was dissolved in chloroform/methyl alcohol (having a volume ratio of ⅓) and then added with 1 g of NaOH, and the reaction mixture was stirred for 10 min. The stirred reaction solution was washed with an aqueous solution of 1 N HCl, and the organic layer was dried and purified using silica gel column chromatography, thus yielding 0.95 g of the derivative IIc.

Analysis of the derivative A material produced the following NMR data: 1H NMR (300 MHz, CDCl$_3$), δ(ppm) 0.88 (t, 6H, J=6.5 Hz), 1.23-1.50 (m, 20H), 1.64-1.69 (m, 4H), 2.78 (t, 4H, J=7.6 Hz), 3.37 (s, 2H), 7.03-7.08 (m, 6H), 7.25, (d, 2H), 7.60 (s, 2H).

EXAMPLE 1

Fabrication of an Example Organic Semiconductor Thin Film

On a washed plastic substrate, aluminum/niobium (Al/Nb) alloy, serving as a gate electrode, was deposited to a thickness of 1000 Å using a sputtering process, and then SiO$_2$ serving as a gate insulating film, was deposited to a thickness of 1000 Å using a CVD process.

Figure 8:
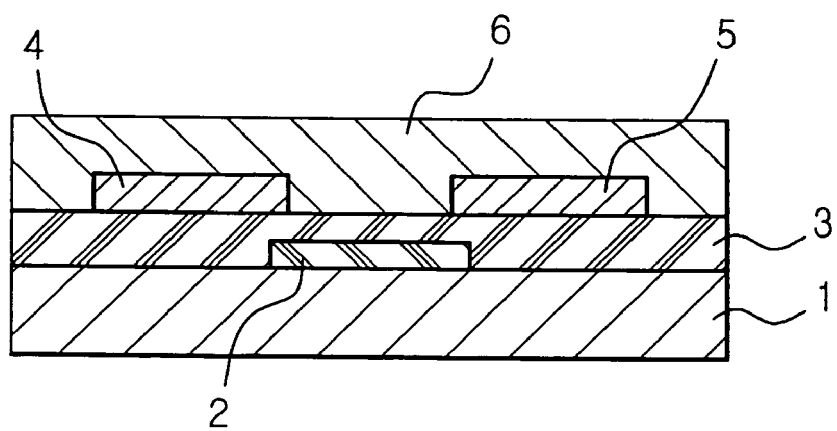
FIG. 8 is a schematic cross-sectional view showing an example embodiment of an organic thin film transistor.

Subsequently, Au, serving as source-drain electrodes, was deposited to a thickness of 1200 Å using a sputtering process. Before the substrate was deposited with the organic semiconductor material, it was washed using isopropyl alcohol for 10 min and then dried. The substrate was then immersed in a 10 mM solution of octadecyltrichlorosilane in hexane for 30 seconds, washed with acetone, and then dried Example aromatic enediyne derivative A obtained above in Preparative Example 1 was dissolved at a concentration of 0.1 wt % in a xylene solvent and then applied to the prepared substrate using a spin coating process to form a coating film. The coating film was then baked at 150° C. for 30 minutes in an argon atmosphere, thereby manufacturing the bottom-contact-type organic thin film transistor generally corresponding to the structure illustrated in FIG. 8.

EXAMPLES 2 TO 6

Fabrication of Additional Example Organic Thin Film Transistors

Respective organic thin film transistors were manufactured in the same manner as detailed above in connection with Example 1, with the exception that each example aromatic enediyne derivatives B, C and D synthesized in the corresponding Preparative Examples 2 to 6 was used as the material for forming the organic active layer.

The organic active layers formed using example aromatic enediyne derivatives synthesized in Preparative Examples 1 to 4 were then measured for DSC. The results of these measurements are shown in FIGS. 1 to 4.

As shown in FIGS. 1 to 4, each example aromatic enediyne derivative was found to begin crosslinking at about 120° C. and then to actively react at 200° C. or lower. As is apparent from these results, aromatic enediyne derivatives according to example embodiments may be successfully converted into a semiconductor thin film using relatively low-temperature, solution-based wet processes.

Figure 5:
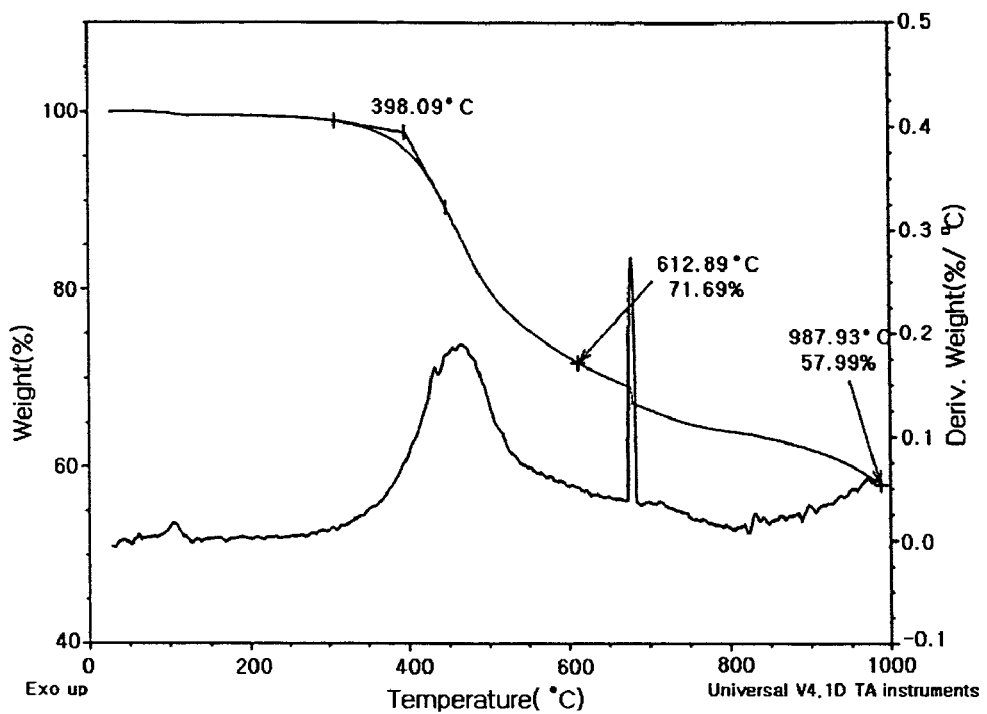
FIG. 5 is a graph showing the result of a thermogravimetry analysis (TGA) of an example embodiment of an aromatic enediyne derivative as synthesized in Preparative Example 1 below.
Figure 6:
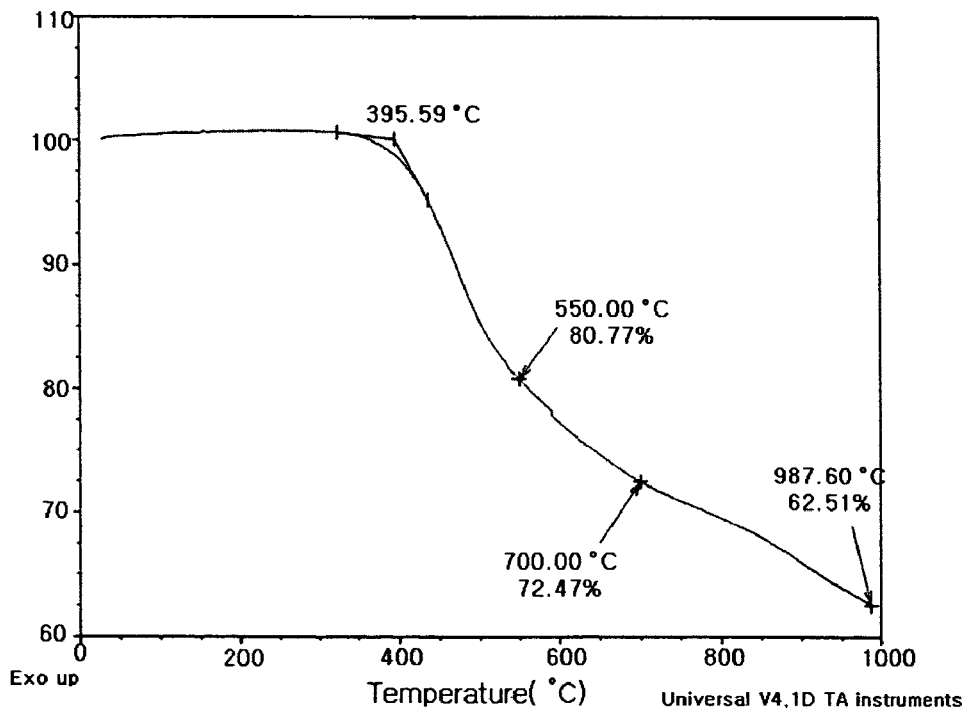
FIG. 6 is a graph showing the result of TGA of an example embodiment of an aromatic enediyne derivative as synthesized in Preparative Example 2 below.

The TGA of example aromatic enediyne derivatives obtained in Preparative Examples 1 and 2 was measured with the results shown in FIGS. 5 and 6.

As reflected in FIGS. 5 and 6, example aromatic enediyne derivatives exhibited no weight loss up to about 300° C. That example aromatic enediyne derivatives did not lose weight even at temperatures exceeding the reaction temperature of 120 to 160° C. indicates that no more gas was being generated from or in the resulting polymer. Therefore, in the case where the semiconductor thin film is formed using aromatic enediyne derivatives according to example embodiments, the cracking problem of the resulting thin films due to the generation of gas within the film may be suppressed or prevented.

Figure 7:
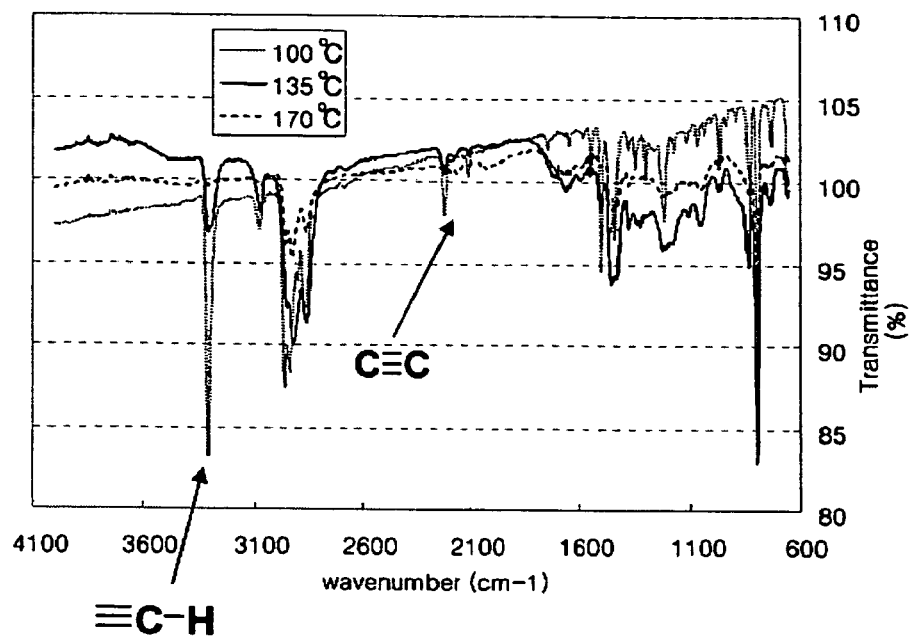
FIG. 7 is an IR spectrum of an example embodiment of an organic semiconductor thin film as manufactured in Example 1 below.

In an example organic semiconductor thin film manufactured in Example 1, IR measurements were taken to explore changes in structure of the organic semiconductor thin film as a function of temperature. The results of this evaluation are presented in FIG. 7 and which indicate that the peaks corresponding to triple bonded carbon (C≡C) and hydrogen bonds associate with a triple bonded carbon (≡C—H) were reduced as the annealing temperature was increased. This result may be attributed to the formation of benzene rings and the realization of polymerization according to the active mechanism of enediyne when the temperature was increased.

In order to evaluate the electrical properties of example organic thin film transistors fabricated in Examples 1 to 4, current transfer properties were measured using a semiconductor characterization system (4200-SCS), available from KEITHLEY Co. Ltd., from which charge mobility and cut-off leakage current were then calculated for each sample. The results are given below in TABLE 1. The charge mobility was calculated using the above current transfer curve and the following current equation for the saturation region. That is, the current equation for the saturation region was converted into a graph relating $(I_{SD})^{1/2}$ to $V_G$, and the charge mobility was calculated from the slope of the converted graph:

$$I_{SD} = \frac{WC_O}{2L}\mu(V_G - V_T)^2$$

-continued $$\sqrt{I_{SD}} = \sqrt{\frac{\mu C_O W}{2L}}(V_G - V_T)$$

$$\text{slope} = \sqrt{\frac{\mu C_O W}{2L}}$$

$$\mu_{FET} = (\text{slope})^2 \frac{2L}{C_O W}$$

wherein $I_{SD}$ is source-drain current; $\mu$ or $\mu_{FET}$ is charge mobility; $C_O$ is oxide film capacitance; W is channel width; L is channel length; $V_G$ is gate voltage; and $V_T$ is threshold voltage.

The cut-off leakage current ($I_{off}$), which is the current flowing with the transistor in the off-state, was determined to be the minimum current in the off-state.

TABLE 1

| Organic Active Layer | Charge Mobility (cm²/V-s) | Cut-off Leakage Current (A) |
|---|---|---|
| Ex. 1 | $7 \times 10^{-5}$ | $10^{-11}$ |
| Ex. 2 | $5 \times 10^{-4}$ | $10^{-10}$ |
| Ex. 3 | $8 \times 10^{-3}$ | $5 \times 10^{-11}$ |
| Ex. 4 | $5 \times 10^{-4}$ | $10^{-11}$ |
| Ex. 5 | $6 \times 10^{-3}$ | $10^{-11}$ |
| Ex. 6 | $8 \times 10^{-4}$ | $10^{-10}$ |

As is apparent from the data presented in TABLE 1, the transistors manufactured using aromatic enediyne derivatives according to example embodiments exhibited very low cut-off leakage currents of $10^{-10}$ A or less while maintaining the performance thereof. Therefore, when aromatic enediyne derivatives according to example embodiments are applied to various electronic devices, for example, thin film transistors, electroluminescent devices, solar cells, and memory, the resulting organic semiconductor thin film may exhibit improved electrical properties.

As described above, example embodiments include aromatic enediyne derivatives, organic semiconductor thin films formed using such aromatic enediyne derivatives, methods of manufacturing such organic semiconductor thin films, and methods of manufacturing electronic device incorporating such organic semiconductor thin films. Example embodiments of aromatic enediyne derivatives, which are lower molecular organic semiconductor materials, may be applied using a wet process at room temperature and may be utilized in semiconductor processes requiring the formation of organic semiconductor thin films across large process areas. Moreover, the resulting organic semiconductor thin films fabricated from such aromatic enediyne derivatives may exhibit improved chemical and/or electrical stability as well as a regular molecular arrangement that tends to increase resistance to outgassing and associated cracking during the thermal processing to form the organic semiconductor thin films.

Organic semiconductor compounds according to example embodiments may be utilized in various fields including the fabrication of organic thin film transistors, electroluminescent devices, solar cells, and memory devices.

Although example embodiments have been disclosed for illustrative purposes, those skilled in the art will appreciate that various modifications, additions and substitutions are possible, without departing from the scope and spirit as defined in the following claims.

What is claimed is:

1. An aromatic enediyne derivative having a structure according to

Formula I:

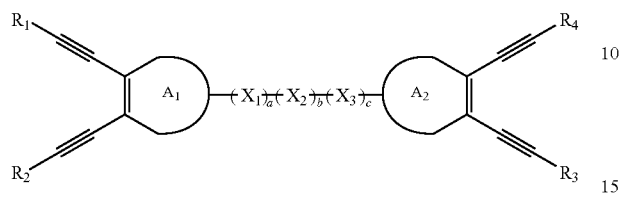

(I)

wherein $X_1$, $X_2$, $X_3$, $A_1$, and $A_2$ are each thiophene;
wherein $R_1$, $R_2$, $R_3$ and $R_4$ are each independently selected from the group consisting of an amino group, a cyano group, —$SiR^1R^2R^3$ (where $R^1$, $R^2$, and $R^3$ are each independently selected from a group consisting of hydrogen and $C_1$-$C_{10}$ alkyl groups), $C_1$-$C_{20}$ alkyl groups; and
further wherein a and b are 1, c is selected from integers from 0 to 2 inclusive, and the expression a+b+c>0 is satisfied;

Formula II:

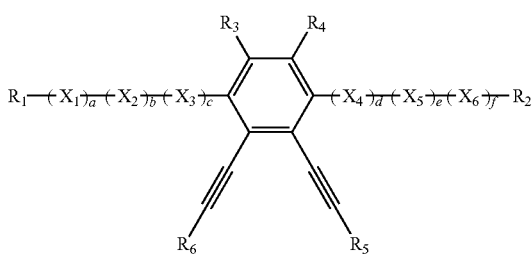

(II)

wherein $X_1$, $X_2$, $X_3$, $X_4$, $X_5$, and $X_6$ are each thiophene,
$R_1$, $R_2$, $R_3$, $R_4$, $R_5$, and $R_6$ are each independently selected from the group consisting of hydrogen, an amino group, a cyano group, and $C_1$-$C_{20}$ alkyl groups; and
further wherein a b, c, d, e and f are selected from integers from 0 to 1 inclusive, and the expression $3 \leq a+b+c+d+e+f \leq 5$ is satisfied; or Formula III:

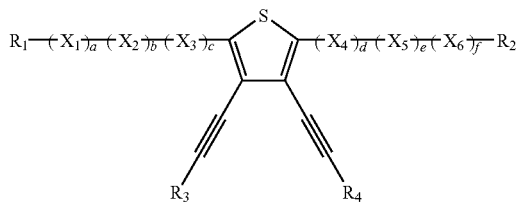

(III)

wherein $X_1$, $X_2$, $X_3$, $X_4$, $X_5$, and $X_6$ are each thiophene,
$R_1$, $R_2$, $R_3$, and $R_4$ are each independently selected from the group consisting of hydrogen, an amino group, a cyano group, —$SiR^1R^2R^3$ (where $R^1$, $R^2$, and $R^3$ are each independently hydrogen or a $C_1$-$C_{10}$ alkyl group), and $C_1$-$C_{20}$ alkyl groups; and
further wherein a, b, c, d, e and f are selected from integers from 0 to 1 inclusive, and the expression $3 \leq a+b+c+d+e+f \leq 5$ is satisfied.

2. The enediyne derivative according to claim 1, wherein:
the enediyne derivative has a structure corresponding to Formula V or Formula VI

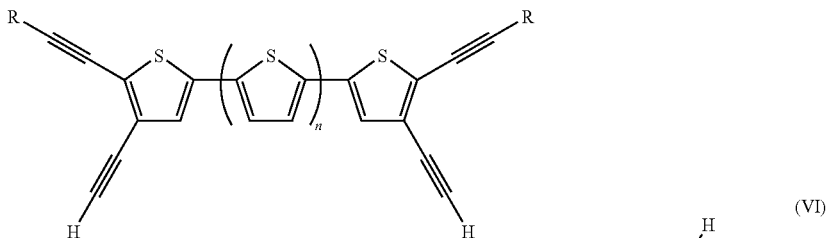

(V)

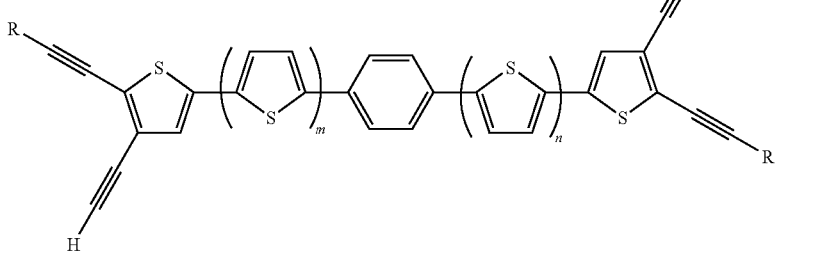

(VI)

wherein R is selected from a group consisting of an amino group, a cyano group, —SiR$^1$R$^2$R$^3$, wherein R$^1$, R$^2$, and R$^3$ are each independently selected from a group consisting of hydrogen and C$_1$-C$_{10}$ alkyl groups, C$_1$-C$_{20}$ alkyl groups, where the n of Formula V is 2-4, and in Formula VI n is 1 and m is 1.

* * * * *